United States Patent
Dubey et al.

(10) Patent No.: US 10,722,327 B2
(45) Date of Patent: Jul. 28, 2020

(54) HIGH VOLUME CARTRIDGE AND MATERIAL DELIVERY SYSTEM

(71) Applicant: Centrix, Inc., Shelton, CT (US)

(72) Inventors: Ryan Dubey, Meriden, CT (US); David Saily, Ridgefield, CT (US)

(73) Assignee: Centrix, Inc., Shelton, CT (US)

( * ) Notice: Subject to any disclaimer, the term of this patent is extended or adjusted under 35 U.S.C. 154(b) by 132 days.

(21) Appl. No.: 15/934,685

(22) Filed: Mar. 23, 2018

(65) Prior Publication Data

US 2018/0280115 A1   Oct. 4, 2018

Related U.S. Application Data

(60) Provisional application No. 62/477,983, filed on Mar. 28, 2017.

(51) Int. Cl.
| | | |
|---|---|---|
| *A61C 5/62* | (2017.01) | |
| *A61B 17/88* | (2006.01) | |
| *A61M 5/31* | (2006.01) | |
| *A61M 5/315* | (2006.01) | |

(52) U.S. Cl.
CPC ............ *A61C 5/62* (2017.02); *A61B 17/8825* (2013.01); *A61B 17/8833* (2013.01); *A61M 5/3134* (2013.01); *A61M 5/3135* (2013.01); *A61M 5/31513* (2013.01); *A61M 2005/3142* (2013.01)

(58) Field of Classification Search
CPC .................................... A61C 5/62; A61C 5/66
See application file for complete search history.

(56) References Cited

U.S. PATENT DOCUMENTS

| | | | |
|---|---|---|---|
| 5,489,207 A | 2/1996 | Dragan et al. | 433/90 |
| 5,620,423 A * | 4/1997 | Eykmann | A61M 5/31513 604/218 |
| 8,616,879 B2 | 12/2013 | Dubey et al. | 433/80 |
| 8,834,158 B2 * | 9/2014 | Leiner | A61M 5/31583 433/90 |
| 2007/0228076 A1 * | 10/2007 | Horner | A61C 9/0026 222/135 |
| 2017/0027662 A1 * | 2/2017 | Sobina | B29C 65/08 |
| 2017/0027663 A1 * | 2/2017 | Pauser | B05C 17/00503 |

* cited by examiner

*Primary Examiner* — Ralph A Lewis
(74) *Attorney, Agent, or Firm* — Fattibene and Fattibene, LLC; Paul A. Fattibene (57) ABSTRACT

A cartridge having a plunger cylinder with an external diameter smaller than a piston cylinder internal diameter. The cartridge has a plunger cylinder adapted to fit within a breach opening of a syringe. The piston cylinder having a larger internal diameter than the external diameter of the plunger cylinder, the cartridge is capable of holding a larger volume of material in the piston cylinder than could be held in the plunger cylinder fitted within the syringe breach opening. A piston placed in the piston cylinder has a concave surface.

11 Claims, 7 Drawing Sheets

HIGH VOLUME CARTRIDGE AND MATERIAL DELIVERY SYSTEM

RELATED APPLICATION

This application claims the benefit of U.S. provisional application No. 62/477,983 filed Mar. 28, 2017.

FIELD OF THE INVENTION

The present invention relates in general to a cartridge for delivering a larger volume of material, and particularly to a cartridge that fits into a syringe intended to hold cartridges for delivering a smaller volume of material.

BACKGROUND OF THE INVENTION

In medical applications it is often necessary to accurately place a quantity of material in precise locations. In dentistry often viscous materials have been used in dental restorations. A syringe having a mechanical advantage has been used to precisely deliver viscous dental materials. One such syringe is disclosed in U.S. Pat. No. 5,489,207 entitled "Dental Cartridge Extruder with Rigid Drop-In Front End" issuing to Dragan et al. on Feb. 6, 1996, which is herein incorporated by reference. Therein disclosed is a syringe having a barrel with a breach opening in the front end for receiving a cartridge containing a dental material. The cartridge has an outer diameter that fits within the breach opening. A plunger pushes a plug or piston within the rear end of the cartridge forcing the material out of a nozzle. The lever advances the plunger with a mechanical advantage to extrude viscous materials.

While this syringe is suitable to dispense relatively small volumes of material precisely there is a need for dispensing larger volumes of material in some applications.

SUMMARY OF THE INVENTION

The present invention is a cartridge that contains a relatively high volume of material that is capable of being placed in a syringe having a mechanical advantage and with a relatively small breach opening. The cartridge has a plunger end with a diameter to fit within the breach opening of a syringe and a piston end with a larger diameter than the plunger end diameter. The piston end having a larger diameter contains a larger volume of material than would be possible to be contained in the plunger end of the cartridge. A plunger is advanced forward towards a nozzle forcing the material from the piston end through the nozzle for placement at a desired location. The plunger end has an external diameter to fit within the breach opening of a syringe and a piston end with a larger internal diameter than the external diameter of the plunger end.

Accordingly, it is an object of the present invention to dispense a large volume of material.

It is an advantage of the present invention that it can fit within a syringe having a breach opening smaller than the piston end containing the material being dispensed.

It is a feature of the present invention that the plunger end has an external diameter smaller than the internal diameter of the piston end.

These and other objects, advantages, and features will become more readily apparent in view the following detailed description.

BRIEF DESCRIPTION OF THE DRAWINGS

FIG. 8 is a perspective view illustrating a syringe with a mechanical advantage which the present invention is used with.

DETAILED DESCRIPTION OF THE PREFERRED EMBODIMENTS

Figure 1:
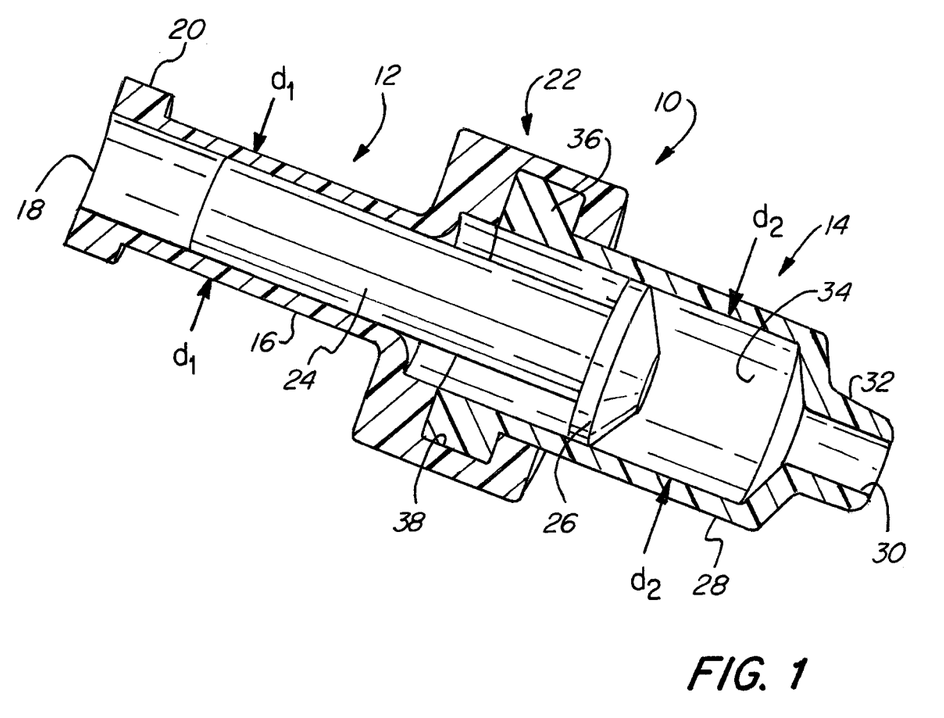
FIG. 1 is a partial section schematically illustrating the present invention.

FIG. 1 is a partial sectioned view illustrating the high volume cartridge 10 of the present invention. The cartridge 10 comprises a plunger end 12 coupled to a piston end 14. The plunger end 12 comprises a plunger cylinder 16 having an external diameter $d_1$ with a plunger bore 18 and a plunger end flange 20 on the rear open end of the bore 18. On the other end opposing the open end having the flanged 20 is a coupling 22. The portion of the coupling 22 formed with the plunger end 12 has a groove 38 formed therein. The piston end 14 comprises a piston cylinder 28 having an internal diameter $d_2$ with a nozzle 32 having a nozzle bore 30 on one end and on the opposing end with a collar 36. The collar 36 mates with the groove 38 attaching the plunger end 12 to the piston end 14 forming the cartridge 10. A plunger 24 placed within the cartridge 10 has a piston 26 on one end. The piston 26 is sized to fit within the cylinder bore 34 of the piston cylinder 28. The plunger 24 is sized to fit within the plunger cylinder bore 18 in the plunger end 12.

Figure 2:
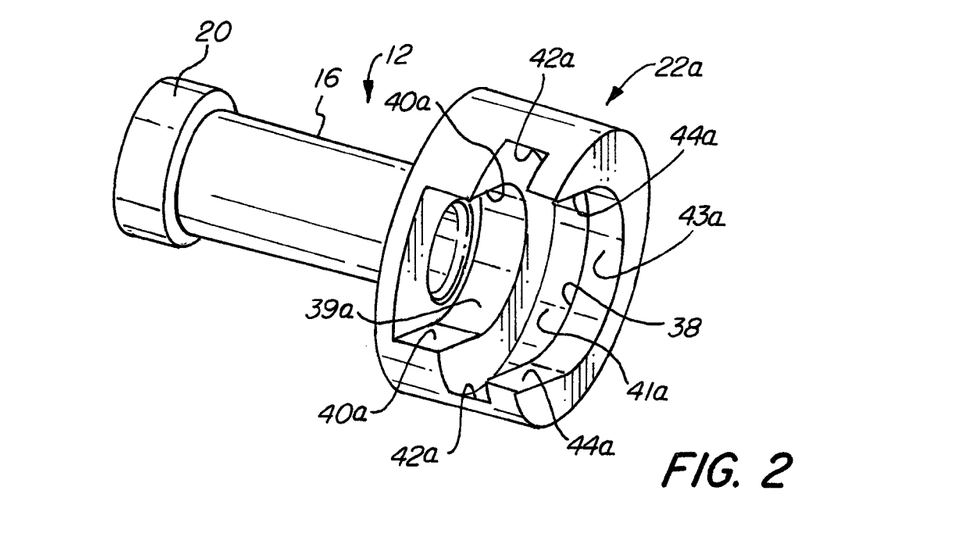
FIG. 2 is a perspective view illustrating the rear plunger end of the present invention.

FIG. 2 is a perspective view illustrating the plunger end 12. FIG. 2 more clearly illustrates the structure of the plunger end coupling portion 22a of the coupling 22 attached to the plunger end 12. This plunger end coupling portion 22a of the coupling 22 has a plunger end groove 38 formed therein. Between one wall of the groove 38 and adjacent the plunger cylinder 16 is a curved surface 39a. The curved surface 39a is place between flat sliding surfaces 40a. Adjacent the opposing wall of the groove 38 there is a curved surface 43a placed between flat sliding surfaces 44a. The groove 38 has a curved surface 41a placed between flat sliding surfaces 42a.

Figure 3:
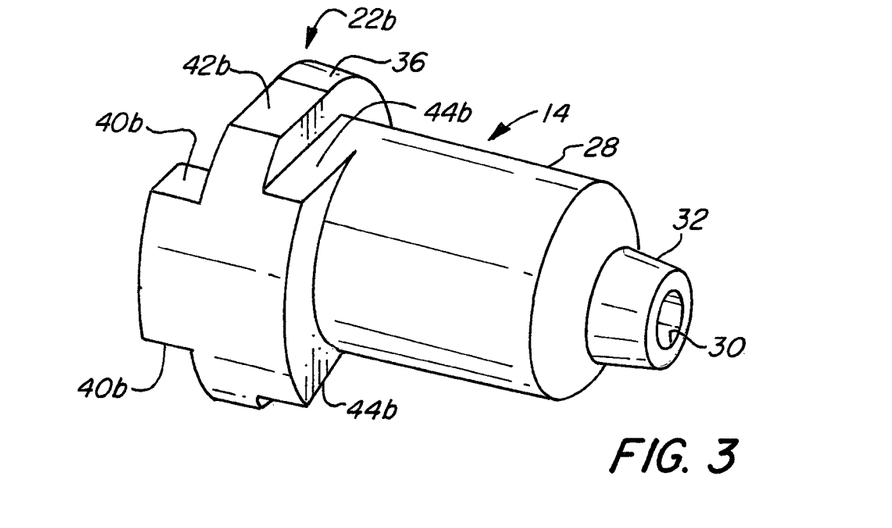
FIG. 3 is a perspective view illustrating the front piston end of the present invention.

FIG. 3 is a perspective view illustrating the piston end 14. FIG. 3 more clearly illustrates the structure of the piston end coupling portion 22b of the coupling 22 attached to the piston end 14. This piston end coupling portion 22b of the coupling 22 has a piston end collar 36 that is sized and adapted to fit within the plunger end groove 38 illustrated in FIG. 2. The collar 36 has mating flat surfaces 42b that mate with the flat sliding surfaces 42a illustrated in FIG. 2. Adjacent one side of the collar 36 are mating flat surfaces 40b and adjacent the other side of the collar 36 are mating flat surfaces 44b. The mating flat surfaces 44b mate with the flat sliding surfaces 44a illustrated in FIG. 2. The mating flat surfaces 40b mate with the flat sliding surfaces 40a illustrated in FIG. 2.

From FIGS. 2 and 3 it can clearly be appreciated and understood how the plunger end 12 is coupled to the piston end 14. The collar 36, illustrated in FIG. 3, is aligned with the groove 38, illustrated in FIG. 2. The piston end 14 is moved laterally relative to the plunger end 12 sliding the plunger end coupling portion 22a and the piston end coupling portion 22b together. Prior to coupling the plunger end 12 to the piston end 14 the plunger 24, illustrated in FIG. 1, is inserted into the plunger cylinder 16 so that the piston 26, illustrated in FIG. 1, resides adjacent the curved surface 39a and does not extend into the groove 38. After assembling or coupling the plunger end 12 and piston end 14 together the piston 26, illustrated in FIG. 1, can be advanced slightly towards the nozzle 32 locking the assembly of the plunger end 12 and piston end 14 together.

Figure 4:
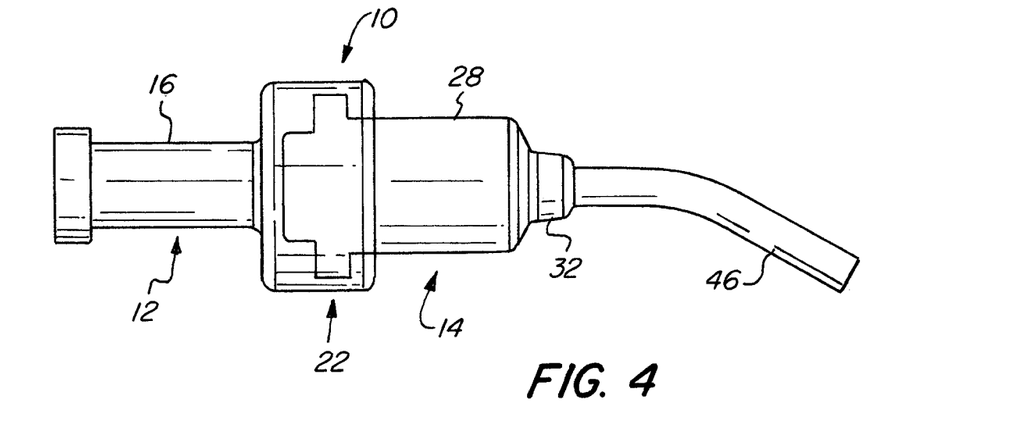
FIG. 4 is a side elevational view illustrating the assembled high volume cartridge of the present invention.

FIG. 4 illustrates the assembled high volume cartridge 10. In FIG. 4 the plunger end 12 and the piston end 14 are coupled together by the coupling 22. A metal cannula 46 is preferably placed within the nozzle 32 facilitating accurate placement of the material to be dispensed.

Figure 5A:
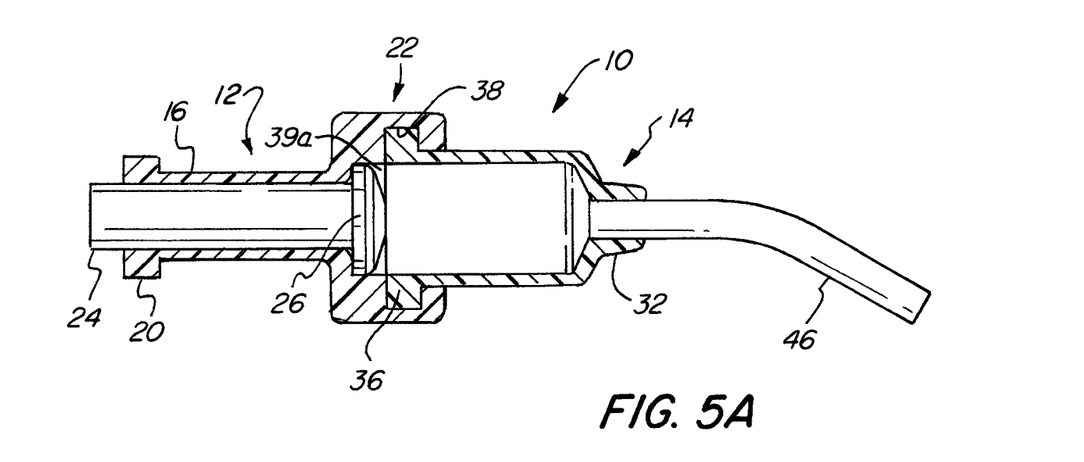
FIGS. 5A-5C illustrates the sequential advancement of the plunger and piston of the present invention.
Figure 5B:
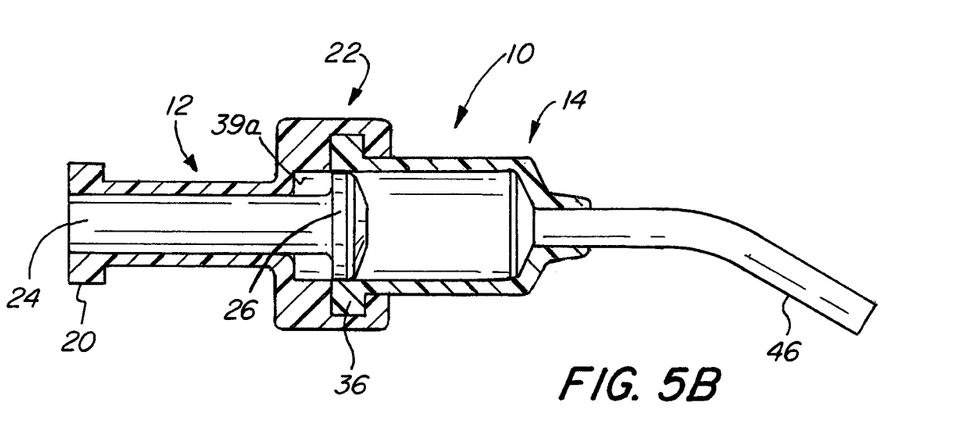
Figure 5C:
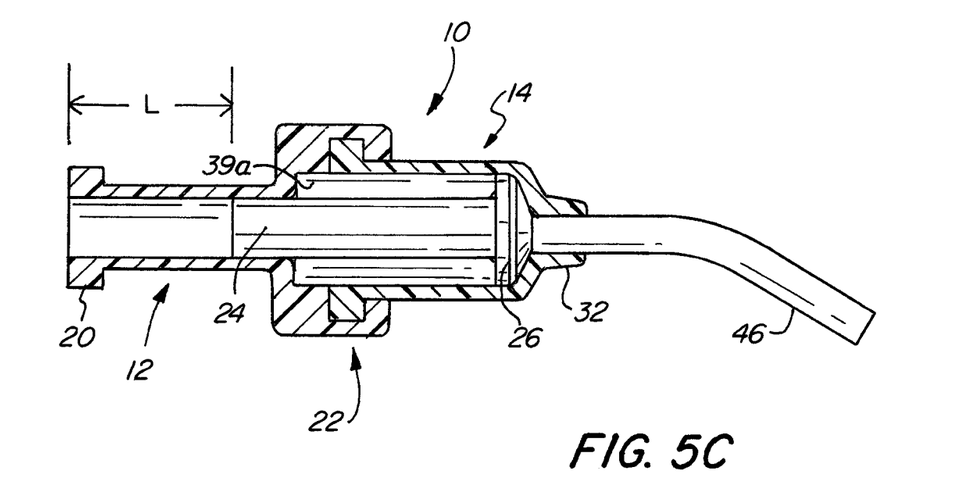

FIGS. 5A-C illustrates the positioning of the plunger 24 and piston 26. FIG. 5A illustrates the positioning of the plunger 24 and the piston 26 so that the piston 26 is positioned adjacent to the curved surface 39a of the plunger end 12. This permits the piston end 14 and the piston end collar 36 to be slid laterally into the plunger end groove 38. After the plunger cylinder bore 18 and the piston cylinder bore 34 are coaxially positioned the piston 26 and the plunger 24 are moved forward towards the nozzle 32 locking the assembled high volume cartridge 10 together. FIG. 5B illustrates the movement of the piston 26 beyond the curved surface 39a and into the piston end 14. FIG. 5C illustrates the piston 26 advanced to the end of its travel adjacent to the nozzle 32. The distance L represents the stroke or distance of travel from the end of the collar 20 to the rear end of the plunger 24.

Figure 6:
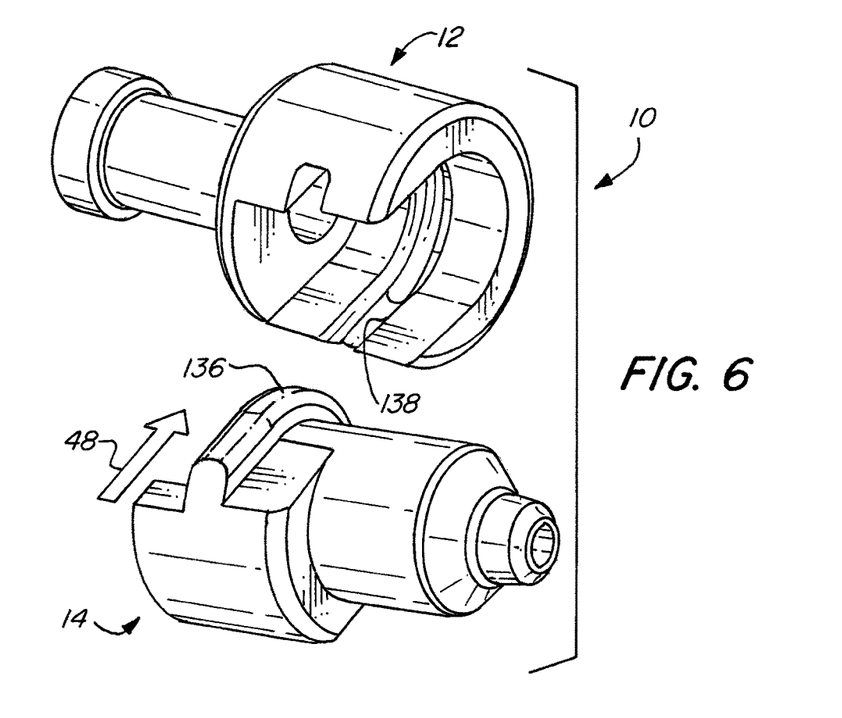
FIG. 6 is a perspective view schematically illustrating the assembly of the rear plunger end and the front piston end components of the high volume cartridge of the present invention.

FIG. 6 schematically illustrates the assembly of the high volume cartridge 10. The plunger end 12 and the piston end 14 are moved laterally together in the direction of the arrow 48. The embodiment illustrated in FIG. 6 has a slightly different shaped collar 136 and groove 138 that has a more rounded or angled shape. The collar 136 and the groove 138 may have different mating shapes to facilitate assembly and a secure coupling.

Figures 7A, 7B, 7C:
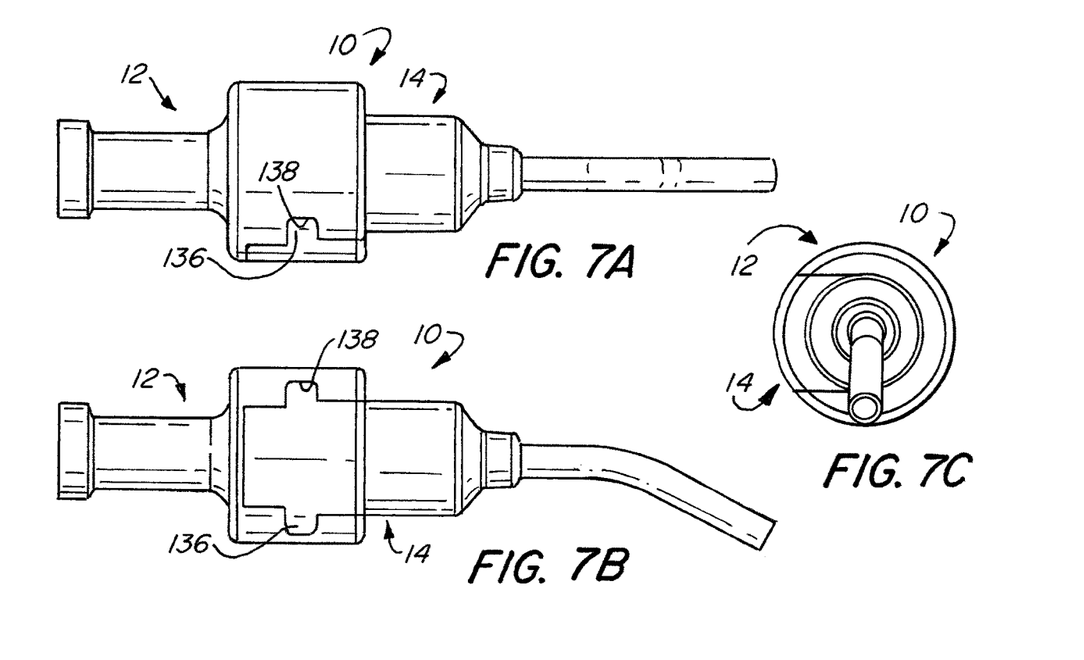
FIG. 7A is a plan view of the assembled high volume cartridge of the present invention.
FIG. 7B is a side elevational view of the assembled high volume cartridge of the present invention.
FIG. 7C is a front end elevational view of the assembled high volume cartridge of the present invention.

FIGS. 7A-C illustrate different views of the high volume cartridge 10 that clearly illustrate the structure of the assembled plunger end 12 and piston end 14 forming the high volume cartridge 10.

Figure 8:
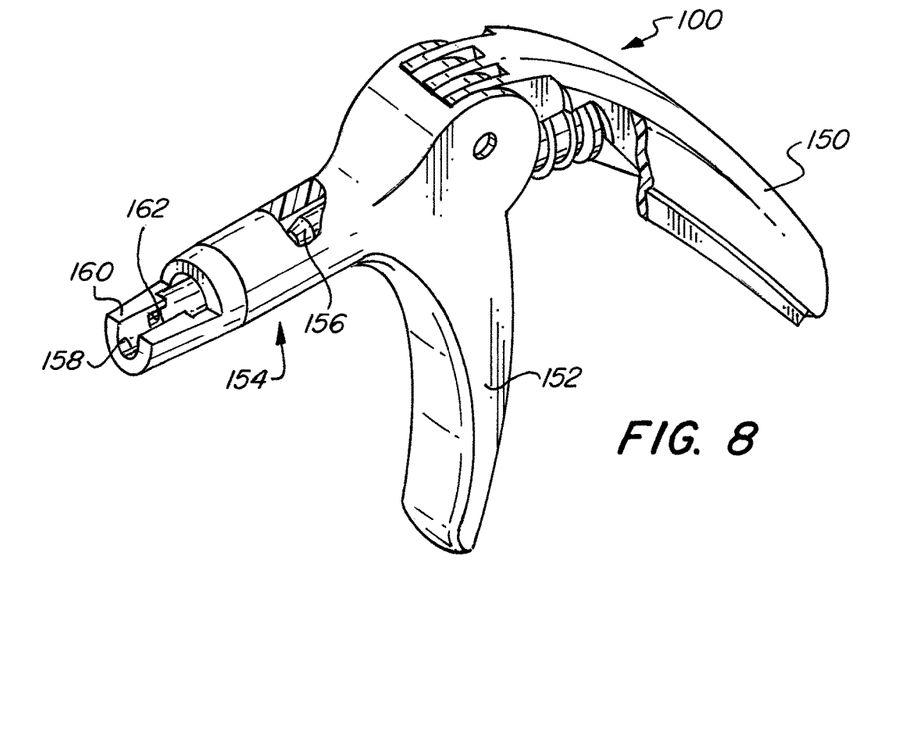

FIG. 8 is a perspective view illustrating a syringe gun 100 use with the high volume cartridge 10 of the present invention. The syringe gun 100 may be similar to the dental cartridge extruder disclosed in U.S. Pat. No. 5,489,207 issuing Feb. 6, 1996 to Dragon et al., which is herein incorporated by reference, or other similar syringe. The syringe gun 100 has a lever 150 and a handle 152 connected to a barrel 154. A syringe plunger 156 reciprocally moves within the barrel 154. The end of the barrel 154 has a breach opening 158 with sidewalls 160. A flanged retainer 162 may be formed in the rear of the breach opening 158.

Figure 9:
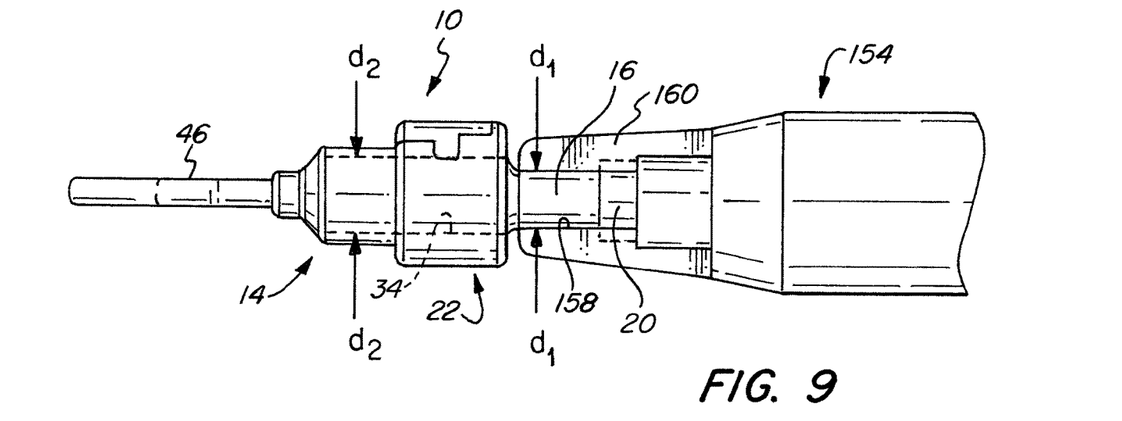
FIG. 9 is a plan view illustrating the present invention placed within the breach opening of the syringe illustrated in FIG. 8.

FIG. 9 illustrates the high volume cartridge 10 having its plunger end with the plunger cylinder 16 securely placed within the breach opening 158 of the syringe gun. As illustrated in FIG. 9, the plunger cylinder external diameter $d_1$ is smaller than the piston cylinder internal diameter $d_2$ of the plunger cylinder 34.

Figure 10:
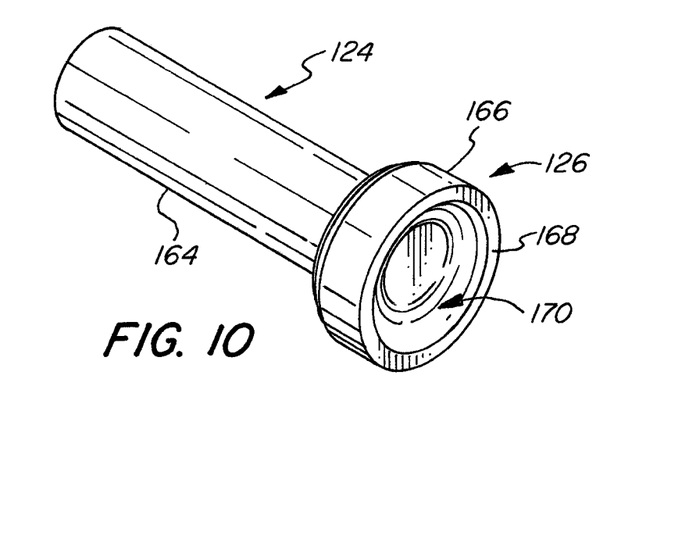
FIG. 10 is a perspective view of another embodiment of a plunger.
Figure 11:
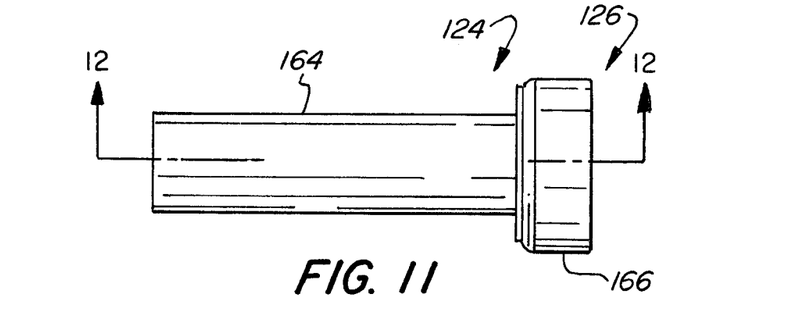
FIG. 11 is an elevational view of the embodiment illustrated in FIG. 10.
Figure 12:
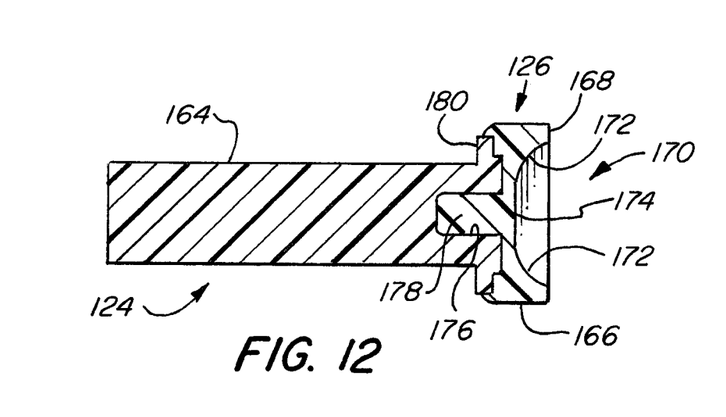
FIG. 12 is a cross section taken along line 12-12 in FIG. 11.

FIGS. 10-12 illustrate another embodiment of a plunger particularly suited for placement of high viscosity materials, such as used in bone grafting. Bone grafting is used to replace missing bone. In some applications a synthetic bone graft material is formulated with hydroxyapatite mixed with bone marrow. Bone grafts are often used in dental procedures, as well as other medical procedures to replace missing bone. The bone grafting material may have a putty like constancy that is very viscous. A plunger assembly 124 has a shaft 164 and a piston 126. The piston 126 has a piston sidewall 166 having a front lip 168 and a concave surface 170.

FIG. 12 is a cross section of the plunger assembly 124 more clearly illustrating the structure of the plunger assembly 124 and the shape of the concave surface 170. The shaft 164 has a bore 176 therein and a stepped flange 180 on one end. The rear end of the piston 126 has a surface conforming to the stepped flange 180 in an insert 178 shape to fit within the bore 176. The stepped flange 180 has an outer diameter slightly less than the outer diameter of the piston 126 so that the piston sidewall 166 extends beyond the stepped flange 180. The concave surface 170 has a radius portion 172 and a flat portion 174 surrounded by the radius portion 172. The radius portion 172 may be spherical. The piston 126 is preferably made of a flexible elastic yet rigid material such as a hard rubber or soft plastic. The shaft 164 maybe made of any rigid material, but is preferably a hard plastic.

This embodiment of the plunger assembly 124 has the advantage that when extruding highly viscous materials a component of force is applied to the radius portion 172 that will generate a radial force forcing the piston side wall 166 against the internal surface of the piston cylinder bore 34, illustrated in FIG. 1. This improves the seal between the piston sidewall 166 and the surface of the piston cylinder bore 34, illustrated in FIG. 1, preventing the highly viscous material being extruded from being forced behind or leaking behind the piston 126.

It should readily be appreciated that the high volume cartridge 10 can extrude or dispense a higher volume of material over the same stroke of the plunger 24 when pushed by the syringe plunger 156 due to the larger diameter of the piston cylinder bore 34 relative to the plunger cylinder bore 18. This makes possible the use of a standard or commonly available syringe gun 100 with cartridges that contain and dispense a higher volume of material than previously possible.

The high-volume dental cartridge 10 of the present invention is suitable for delivering precise and relatively high volumes of material in many medical applications. The present invention is particularly well-suited for delivery of relatively viscous materials, and in particular dental materials. The present invention may also be used for the precise placement of synthetic bone and other materials in medical applications.

While the invention has been described with respect to several embodiments, other variations and modifications may be made without departing from the spirit or scope of the invention.

What is claimed is:

1. A cartridge for dispensing a material comprising:
a plunger cylinder having a first external diameter and having a first bore with a first internal diameter;
a plunger end coupling portion placed on one end of said plunger cylinder, said plunger end coupling portion having a side wall opening and a plunger end groove between a first curved surface and a second curved surface, wherein the plunger end groove ends at the side wall opening forming a lateral breach opening;
a plunger placed within the first bore of said plunger cylinder;
a piston connecting to one end of said plunger, said piston having a second external diameter larger than the first internal diameter; and
a piston cylinder having a second bore with a second internal diameter, said second internal diameter being larger than the first external diameter of said plunger cylinder, the second bore of said piston cylinder coaxially coupled to the first bore of said plunger cylinder, and said piston placed within the second bore of said piston cylinder;
a piston end coupling portion placed on one end of said piston cylinder, said piston end coupling portion having a piston end collar sized and adapted to fit within the plunger end groove through the lateral breach opening of said plunger end coupling portion,
whereby a volume of material may be dispenses from the second bore with said plunger.

2. The cartridge as in claim 1 further comprising:
a material placed within the second bore of said piston cylinder.

3. The cartridge as in claim 2 wherein:
said material comprises a dental material.

4. The cartridge as in claim 2 wherein:
said material comprises a synthetic bone material.

5. The cartridge for dispensing a material as in claim 1 wherein:
said piston has a concave surface.

6. The cartridge for dispensing a material as in claim 5 wherein:
the concave surface comprises a radius portion surrounding a flat surface.

7. A syringe and cartridge for dispensing a material comprising:
a syringe having a barrel with a breach opening;
a cartridge comprising;
a plunger cylinder having a first external diameter and having a first bore with a first internal diameter;
a plunger end coupling portion placed on one end of said plunger cylinder, said plunger end coupling portion having a side wall opening and a plunger end groove between a first curved surface and a second curved surface, wherein the plunger end groove ends at the side wall opening forming a lateral breach opening;
a plunger placed within the first bore of said plunger cylinder, said plunger having a plunger end with a size to fit within the breach opening of said syringe;
a piston connecting to one end of said plunger and having a piston end, said piston having a second external diameter larger than the first internal diameter;
a piston cylinder having a second bore with a second internal diameter, said second internal diameter being larger than the first external diameter of said plunger cylinder, the second bore of said piston cylinder coaxially coupled to the first bore of said plunger cylinder, and said piston placed within the second bore of said piston cylinder; and
a piston end coupling portion placed on one end of said piston cylinder, said piston end coupling portion having a piston end collar sized and adapted to fit within the plunger end groove through the lateral breach opening of said plunger end coupling portion,
whereby a volume of material may be dispenses from the piston bore with said plunger.

8. The syringe and cartridge as in claim 7 further comprising:
a bone grafting material placed within said cartridge.

9. The syringe and cartridge as in claim 7 wherein:
the piston end has a concave surface.

10. The syringe and cartridge as in claim 9 wherein:
the concave surface comprises a radius portion surrounding a flat surface.

11. A cartridge for dispensing a material comprising:
a plunger cylinder having a first external diameter and having a first bore with a first internal diameter;
a plunger end coupling portion placed on one end of said plunger cylinder, said plunger end coupling portion having a side wall opening and a plunger end groove between a first curved surface and a second curved surface, the first and second curved surfaces having a flat sliding surface formed at each end of the first and second curved surfaces, wherein the plunger end groove and the flat sliding surfaces end at the side wall opening forming a lateral breach opening;
a plunger placed within the first bore of said plunger cylinder;
a piston connecting to one end of said plunger, said piston having a second external diameter larger than the first internal diameter of said plunger cylinder;
a piston cylinder having a second bore with a second internal diameter, said second internal diameter being larger than the first external diameter of said plunger cylinder, the second bore of said piston cylinder coaxially coupled to the first bore of said plunger cylinder, and said piston placed within the second bore of said piston cylinder; and
a piston end coupling portion placed on one end of said piston cylinder, said piston end coupling portion having a piston end collar placed between mating flat surfaces, the piston end collar sized and adapted to fit within the plunger end groove and the mating flat surfaces sized and adapted to mate with the flat sliding surfaces of said plunger end coupling portion ending at the side wall opening forming the lateral breach opening,
whereby said piston end coupling portion is capable of being joined laterally to said plunger end coupling portion and movement of said plunger locks said piston end coupling portion and said plunger end coupling portion together forming the cartridge so that a volume of material may be dispensed from the second bore with movement of said plunger.

* * * * *